(12) United States Patent
Nikutowski et al.

(10) Patent No.: US 6,528,555 B1
(45) Date of Patent: Mar. 4, 2003

(54) ADHESIVE FOR USE IN THE ORAL ENVIRONMENT HAVING COLOR-CHANGING CAPABILITIES

(75) Inventors: Enrique A. Nikutowski, Austin, TX (US); Darrell S. James, Covina, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 22 days.

(21) Appl. No.: 09/689,019

(22) Filed: Oct. 12, 2000

(51) Int. Cl.$^7$ .............................................. A61K 6/08
(52) U.S. Cl. ..................... 523/116; 523/115; 523/117; 523/118; 523/120; 524/492; 524/493; 524/494
(58) Field of Search ................................. 524/492, 493, 524/494; 523/115, 116, 117, 118, 120

(56) References Cited

U.S. PATENT DOCUMENTS

| | | | |
|---|---|---|---|
| 3,066,112 A | 11/1962 | Bowen | 260/41 |
| 3,539,533 A | 11/1970 | Lee et al. | 260/47 |
| 3,629,187 A | 12/1971 | Waller | 260/41 R |
| 3,709,866 A | 1/1973 | Waller | 260/27 R |
| 3,729,313 A | 4/1973 | Smith | 96/27 R |
| 3,741,769 A | 6/1973 | Smith | 96/35.1 |
| 3,751,399 A | 8/1973 | Lee et al. | 260/47 UA |
| 3,766,132 A | 10/1973 | Lee et al. | 260/41 A |
| 3,808,006 A | 4/1974 | Smith | 96/88 |
| 3,860,556 A | 1/1975 | Taylor | 260/42.52 |
| 4,002,669 A | 1/1977 | Gross et al. | 260/486 B |
| 4,012,840 A | 3/1977 | Takeuchi et al. | |
| 4,071,424 A | 1/1978 | Dart et al. | 204/159.15 |
| 4,115,346 A | 9/1978 | Gross et al. | 260/42.15 |
| 4,150,012 A | 4/1979 | Joos | |
| 4,250,053 A | 2/1981 | Smith | 252/426 |
| 4,259,117 A | 3/1981 | Yamauchi | 106/35 |
| 4,292,029 A | 9/1981 | Craig et al. | 433/228 |
| 4,308,190 A | 12/1981 | Walkowiak et al. | 260/29.7 |
| 4,327,014 A | 4/1982 | Kawahara et al. | 523/116 |
| 4,379,695 A | 4/1983 | Orlowski et al. | 433/217 |
| 4,387,240 A | 6/1983 | Berg | 556/440 |
| 4,394,403 A | 7/1983 | Smith | 427/42 |
| 4,404,150 A | 9/1983 | Tsunekawa et al. | 260/927 R |
| 4,503,169 A | 3/1985 | Randklev | 523/117 |
| 4,642,126 A | 2/1987 | Zador et al. | 51/295 |
| 4,652,274 A | 3/1987 | Boettcher et al. | 51/298 |
| 4,695,251 A | 9/1987 | Randklev | 433/8 |
| 4,737,593 A | 4/1988 | Ellrich et al. | 568/15 |
| 4,772,530 A | 9/1988 | Gottschalk et al. | 430/138 |
| 4,871,786 A | 10/1989 | Aasen et al. | 523/113 |
| 4,874,450 A | 10/1989 | Gottschalk et al. | 156/275.5 |
| 4,954,414 A | 9/1990 | Adair et al. | 430/138 |
| 5,015,180 A | 5/1991 | Randklev | 433/9 |
| 5,055,372 A | 10/1991 | Shanklin et al. | 430/138 |
| 5,057,393 A | 10/1991 | Shanklin et al. | 430/138 |
| 5,172,809 A | 12/1992 | Jacobs et al. | 206/368 |
| 5,221,202 A | 6/1993 | James | 433/9 |
| 5,228,907 A | 7/1993 | Eppinger et al. | 106/35 |
| 5,269,682 A | 12/1993 | Kesling | 433/24 |
| 5,328,363 A | 7/1994 | Chester et al. | 433/9 |
| 5,332,429 A | 7/1994 | Mitra et al. | 106/35 |
| 5,348,154 A | 9/1994 | Jacobs et al. | 206/369 |
| 5,354,199 A | 10/1994 | Jacobs et al. | 433/9 |
| 5,538,129 A | 7/1996 | Chester et al. | 206/63.5 |
| 5,545,676 A | 8/1996 | Palazzotto et al. | 522/15 |
| 5,552,177 A | 9/1996 | Jacobs et al. | 427/2.29 |
| 5,583,178 A | 12/1996 | Oxman et al. | |
| 5,596,025 A | 1/1997 | Oxman et al. | |
| 5,639,802 A | 6/1997 | Neckers et al. | |
| 5,762,192 A | 6/1998 | Jacobs et al. | 206/369 |
| 5,971,754 A | 10/1999 | Sondhi et al. | 433/24 |
| 6,085,004 A | 7/2000 | Dower et al. | |
| 6,187,833 B1 | 2/2001 | Oxman et al. | |

FOREIGN PATENT DOCUMENTS

| | | | |
|---|---|---|---|
| EP | 0173567 | 3/1986 | |
| EP | 0 486 774 A1 | 5/1992 | ............ A61K/6/00 |
| EP | 0 486 775 A1 | 5/1992 | .......... A61K/6/083 |
| GB | 2310855 | 9/1997 | |
| JP | SHO 61-44910 | 3/1986 | |
| JP | HEI 11-139920 | 5/1999 | |
| WO | WO 95/14716 | 6/1995 | |

OTHER PUBLICATIONS

Lee Pharmacueticals USA, Technical Bulletin No. 9040–950, Prosthodent® VL–2: Photocuring Crown Base Composite & Restobond™ 3: Dual Dentin–Enamel Bonding Agent, (Apr. 1989).

Product information from Dental Materials Digest—Dentistry's Premier Information Resource, "Protector, Lee Pharmacueticals," retrieved on Jun. 30, 1999). Retrieved from the Internet<URL: http://www.dentaldigest.com>.

Crypsis Product Information Brochure, OREC Corporation (1994).

*Primary Examiner*—Edward J. Cain

(57) ABSTRACT

An adhesive suitable for use in the oral environment is provided. The adhesive comprises a filler, hardenable resin, a hardener, and a colorant, the composition has an initial color prior to exposure to actinic radiation and a final color that is different from the initial color subsequent to the composition being exposed to actinic radiation. The adhesive can be precoated on to orthodontic appliances.

25 Claims, No Drawings

ADHESIVE FOR USE IN THE ORAL ENVIRONMENT HAVING COLOR-CHANGING CAPABILITIES

TECHNICAL FIELD

The present invention relates adhesive suitable for use in the oral environment, such as a patient's mouth. In particular, the adhesive has a vibrant initial color and having the capability of changing to a final color upon exposure to actinic radiation. The initial and final colors are different.

BACKGROUND

Orthodontic treatment involves movement of malpositioned teeth to orthodontically correct positions. Tiny orthodontic appliances, known as brackets, are connected to anterior, cuspid and bicuspid teeth, and an archwire forms a track to guide movement of the teeth to desired positions. In previous years, the orthodontic appliances were connected to teeth by welding or brazing each appliance to a metal band, which was then placed on the desired tooth. But, more recently, it has been preferred to bond the brackets directly to the tooth surface. The direct bonding method minimized the use of metal band thus eliminating the "metallic mouth" appearance that is often associated with orthodontic treatment.

The use of a bonding method can typically require, among other steps, placing an amount of adhesive on the bracket, applying the brackets to the desired, preferably preconditioned teeth, and removing excess adhesive. Conventional orthodontic adhesives are typically clear or contain pigment, which gives the adhesives a white or tooth color. It is desirable that a sufficient but not an excess amount of adhesive is used to bond the brackets to the teeth surface. Excess adhesive on the teeth will eventually be a site for bacteria accumulation. Because orthodontic treatment can last from 18 to 36 months, the bacteria accumulation may damage the teeth and may lead to discoloration of the adhesive, both of which are very undesirable. Removal of the excess adhesive from teeth surfaces can be difficult if there is similarity in the adhesive color and the teeth color, i.e., due to a lack of a contrasting color in the adhesive.

Some skilled in the art have explored the use of color changing adhesive, in particular for orthodontic applications. For example, an orthodontic adhesive having color changing capabilities upon curing by a light source is commercially available from the Orec® Corporation, San Marcos, Calif. The company supplies a product identified as CRYPSIS Color Change Orthodontic Bonding Adhesive (Photocure). As of the filing date, the adhesive is described at Orec's web site (www.orec.com/Pg21.htm) as having an initial yellow color, which allows easy visualization and removal of excess adhesive prior to curing. Once cured, the adhesive turns to tooth-like color.

U.S. Pat. No. 5,545,676 (Palazzotto et al.) discloses a composition useful as a photocurable adhesive, e.g., for orthodontics. The composition comprises (a) free-radically polymerizable monomer and (b) photoinitiator system, soluble in the monomer, comprising photochemically effective amounts of (i) diaryliodonium salt ("iodonium salt"), (ii) sensitizing compound ("sensitizer") capable of absorbing light within the range of wavelengths between about 300 and 1000 nanometers and capable of sensitizing 2-methyl-4,6-bis-(tricholormethyl)-s-triazine, and (iii) electron donor compound. The donor is different from the sensitizer. It is further specified that the donor oxidation potential is $0 < E_{ox}(\text{donor}) \leq E_{ox}(\text{p-dimethoxybenzene})$. Although the patent describes a very useful photoinitiator system, it does not disclose a system or a composition that has color changing capabilities.

A need remains for adhesives that exhibits effective color changing capabilities within a practical working time to aid a dental practitioner in applying orthodontic appliances to a patient's teeth.

SUMMARY

The present invention provides a new adhesive suitable for use in the oral environment. The adhesive is used in orthodontic application. It contains a colorant and optionally a sensitizer to impart color-changing capability. The adhesive provides a vibrant initial color (before actinic radiation exposure) that is remarkably different than dental structures, such as teeth, thereby aiding the practitioner in using a sufficient amount and in placing it in and on areas of the dental structure. Useful initial colors include pink, red, blue, orange, and green, which tends to provide better color contrast against the dental structures, as compared to a yellow colored adhesive. Methods of making and using the color-changing adhesive are also provided.

In brief summary, the present invention is directed to an adhesive for use in the oral environment, the adhesive comprising a filler, a hardenable resin, a hardener, and a colorant, the adhesive having an initial color prior to exposure to actinic radiation and a final color after exposure to actinic radiation. The initial and final colors are different. The inventive adhesive is capable of undergoing a change in color of $\Delta E^*$ greater than about 10 as a result of actinic radiation exposure. In one inventive embodiment, a dye or a combination of dyes can be used to impart a desired initial color.

Advantageously, the adhesive's final color preferably closely matches the dental structures that surrounds it. Alternatively, it is able to transmit the color of the underlying dental structure, i.e., the final color is substantially clear. By formulating the adhesive so that it results in a tooth-like hue, the adhesive can form an "aesthetic" layer upon the tooth surface. Dental materials that match normal tooth color and shades (i.e. tooth-like) are often considered to have high aesthetic quality, especially when the dental material is indistinguishable from the normal tooth surface when viewed from only a short distance.

Another advantage of the present invention is ease of use because the adhesive cures quickly. A practitioner such as an orthodontist can easily cure it using a conventional dental curing light.

The present invention also provides for orthodontic appliances that are precoated with the adhesive, the appliance packaged conveniently in capsule-like containers. The precoated appliance typically has a precise amount of adhesive on its base. Precoated appliances represent a significant advantage to the orthodontists. For example, when it is desired to mount the appliance on a tooth, the appliance is simply removed from the package and directly placed on the tooth surface. There is little need, if any, to remove excess adhesive.

The packaging components used to store the adhesive and precoated orthodontic appliances preferably minimize, if not nearly eliminate, the transmission of visible and near infrared light to the appliances. In this way, the stability of the adhesive, and thus the orthodontic appliance can be maintained for a long period of time, on the order of years.

As used herein the following terms are intended to have the following definitions:

"aesthetic layer", means a layer that is customarily positioned in a visible location on teeth (e.g., the tops of molars, labial surfaces of incisors and cuspids) and is either visible due to the layer being the outermost layer or can be seen through any overlying layer;

"hardenable" is descriptive of a material that can be cured or solidified e.g., by heating to remove solvent, heating to cause polymerization, chemical cross-linking, radiation-induced polymerization or crosslinking, or the like;

"photo-bleach(able)" means a loss of color upon exposure to actinic radiation;

"hardener" means a system that initiates hardening of a resin, and can be used synonymously with "initiator system";

"orthodontic appliance" means any device intended to be bonded to the teeth, including, but not limited to, orthodontic brackets, buccal tubes, lingual buttons, and cleats. The appliance has a base for receiving adhesive and it can be made of metal, plastic, ceramic, and combinations thereof; and "tooth-like" color refers to the broad range of colors and shades of naturally occurring teeth, which can be quantified for example, using the Vita™-shade system (covering the range A1 through D4), a tooth color/shade guide frequently used by dental practitioners.

DETAILED DESCRIPTION OF THE INVENTION

Because the adhesive is used in the oral environment, it must be non-toxic and not irritate soft tissues, such as the gums, tongue, and cheek. It has a vibrant initial color to provide strong color contrast between it and the teeth. The color difference between the tooth color and the initial adhesive color, in terms of $\Delta E^*$, should be at least greater than 40, preferably greater than 45, more preferably greater than 50, and most preferably greater than 55, when the tooth color is set at B1 using the Vita™-shade system.

The adhesive is cured using an actinic light source. The cure time is less than about 60 seconds, preferably less than about 45 seconds, and more preferably, less than about 30 seconds. The adhesive photobleaches. It should not, however, bleach substantially while the orthodontist is working with it under the normal office conditions, i.e., normal lighting, room temperature of about 22° to 26° C., and normal relative humidity of about 35% to 65%. In other words, the adhesive should retain nearly all (at least 80%, preferably 90% as measured using a colorimeter) of its initial color while the orthodontist prepares it. A typical working time could be anywhere from about 5 to 15 minutes per tooth. In the case of precoated orthodontic appliances, the working time would be less than about 5 minutes per tooth.

Each of the adhesive components is described in detail below, as well as the method of making and using the adhesive, and precoated orthodontic appliances.

The amount of filler used, referred to herein as the "loading level" and expressed as a weight percent based on the total weight of the adhesive, will vary depending on the type of filler, the hardenable resin and other adhesive components. Preferably, the filler is present from about 65% to 85%, more preferably from about 70% to 80% by weight based on the total weight of the adhesive.

Fillers may be selected from one or more of any material(s) suitable for use in medical applications, such as fillers currently used in dental restorative compositions and the like. Preferably the filler is finely divided and has a maximum particle diameter of less than about 50 micrometers and an average particle diameter of less than about 10 micrometers. The filler can have a unimodal or polymodal (e.g., bimodal) particle size distribution. The filler can be an inorganic material. It can also be a crosslinked organic material that is insoluble in the hardenable resin, and is optionally filled with inorganic filler. The filler can be radiopaque, radiolucent or nonradiopaque.

Examples of suitable organic filler particles include filled or unfilled pulverized polycarbonates, polyepoxides, and the like.

Examples of suitable inorganic fillers are naturally-occurring or synthetic materials such as quartz, nitrides (e.g., silicon nitride), glasses derived from, for example, Ce, Sb, Sn, Zr, Sr, Ba, and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200"silicas sold by DeGussa and "Cab-O-Sil M5" silica sold by Cabot Corp.).

Preferred filler particles are quartz, submicron silica, and non-vitreous microparticles of the type described in U.S. Pat. No. 4,503,169. Metallic fillers may also be used, such as particulate metal filler made from a pure metal, such as those of Groups IVA, VA, VIA, VIIA, VIII, IIB, or IIB, aluminum, indium, and thallium of Group IIB, and tin and lead of Group IVB, or alloys thereof. Conventional dental amalgam alloy powders, which are typically mixtures of silver, tin, copper, and zinc, can optionally be used. The particulate metallic filler preferably has an average particle size of about 1 to 100 micrometers, more preferably about 1 to 50 micrometers. Mixtures of these fillers are also contemplated, as well as combination fillers made from organic and inorganic materials. Fluoroaluminosilicate glass fillers, either untreated or silanol treated, can be used. These glass fillers have the added benefit of releasing fluoride at the site of dental work when placed in the oral environment.

Optionally, the surface of the filler particles may be treated with a surface treatment, such as a coupling agent, in order to enhance the bond between the filler and the hardenable resin. The coupling agent may be functionalized with reactive curing groups, such as acrylates, methacrylates, epoxies, and the like. Examples of coupling agents include silanes, such as gamma-methacryloxypropyltrimethoxysilane, gamma-mercaptopropyltriethoxysilane, beta-(3,4-epoxycyclohexyl)-ethyltrimethoxysilane, gamma-glycidoxypropyltrimethoxysilane, and the like.

The inventive adhesive has an initial color remarkably different than the dental structures. Color is imparted to the adhesive through the use of a colorant. Preferably, the colorant is a dye. In some embodiments, the sensitizer, a component of the initiator system may provide some color to the adhesive. The sensitizer, however, is not relied solely as the colorant, i.e., it alone is not used to impart a vibrant initial color to the adhesive. Thus, in some embodiments the sensitizer may serve a dual purpose of providing photoactivation and imparting a color to the adhesive.

The colorant makes up about 0.001% but less than about 1%, preferably about 0.01% to 0.1% by weight of the total adhesive weight. The amount of colorant may vary depending on its extinction coefficient, the ability of the human eye to discern the initial color, and the desired color change.

A dye may be a pigment and therefore includes any types of suitable pigments. The colorants should be added in an effective amount to achieve the desired color. For health reasons, food, drug, and cosmetic grade dyes are preferred. At least one of the dyes in the inventive adhesive is reactive or photo-bleachable, in order for the final color to be distinguishable from the initial color. Additional dyes that may or may not be reactive or photo-bleachable can be used to achieve a desired color. Thus, a non-reactive dye may impart a certain color or shade when mixed with a reactive dye to achieve a desired initial color.

The color formation and bleaching characteristics of the photo-bleachable dye varies depending on a variety of factors such as, e.g., acid strength, dielectric constant, polarity, amount of oxygen, and moisture content in the atmosphere. But, the bleaching properties of the dye can be readily determined by irradiating the adhesive and evaluating the change in color. Preferably, at least one colorant is at least partially soluble in the hardenable resin.

Suitable colorants that can impart color to the inventive adhesive include, e.g., methylene blue, amaranth, erythrocin, floxine, rose bengal, acid red, Tartrazine, Sunset Yellow FCF, Fast Green FCF, Brilliant Blue FCF, indigo carmine, phenolphthalain, sulfophthalain, Yale Violet, methyl orange, fluorescene, methyl viologene, indophenol, dimurosbetaine, bromeosin Y, laudamine B, thionine, neutral red, toluidine blue O, indocyanine green, sulfobromophthalain, uranin, lithol rubin B, lake red C, lithol red, tetrachlorotetrabrom fluorescene, brilliant lake red R, deep maroon, toluidine red, tetrabrom fluorescene, fast acid magenta, permanent red, dibromfluorescene, permanent orange, uranine, quinone yellow, WS, alizarin cyanine green F, quinizarine green SS, light green SF yellow, patent blue NA, carbathrene blue, resorcinol brown, alizarin purple SS, brilliant fast scarlet, permanent red F5R, Ponceaux SX, fast red S, oil orange SS, poral yellow 5G, fast light yellow 3G, naphthol green B, Ginea Green B, Sudan Blue B, alizarol purple, naphthol blue black, crocin, crocin blue, orange paprica, chlorophyl, cartamine, safflower yellow, beet red, direct fast yellow GC, direct fast orange, direct fast scarlet 4BS, fast red 6BLL, direct sky blue 5B, direct fast turquoise blue GL, direct copper blue 2B, coprantine green G, direct fast black D, milling yellow O, acid brilliant scarlet 3R, acid violet 5B, azaline direct blue A2G, acid cyanine 6B, acid cyanine SR, acid cyanine green G, milling brown 3G, acid fast black VLG, acid black WA, cation yellow 3G, cation golden yellow GL, cation flavin 10G, cation yellow 5GL, cation orange R, cation brown 3GL, cation pin FG, cation brilliant red 4G, cation red GTL, cation red BLH, cation red 6B, cation red 5B, cation blue GLH, cation navy blue RHL, alizarine, chrome fast blue MB, chrome fast brown KE, chrome black P2B, chrome black T, fast scarlet G base, naphthol AS, naphthol AS-G, vat yellow GCN, vat orange RRTS, indigo, vat blue RSN, vat blue BC, vat brilliant green FFB, vat olive green B, vat olive T, vat brown R, vat gray M, disperse fast yellow G, disperse pink RF, disperse blue FFR, disperse blue green B, disperse yellow 5G, disperse golden yellow GG, disperse yellow RL, disperse yellow 3G, disperse orange B, disperse yellow brown 2R, disperse fast ruby 3B, disperse fast red FB, disperse red FL, disperse red GFL, disperse brilliant pink REL, disperse violet HFRL, disperse blue FB, disperse turquoise blue GL, disperse navy blue 2GL, disperse developer, fluorescent brightener WG, fluorescent brightener ERN, fluorescent brightener AT, fluorescent brighter SA, solvent orange G, solvent fast yellow 3RE, solvent fast red B, solvent fast blue HFL, reactive yellow 3G, reactive orange 2R, reactive red 3B, reactive scarlet 2G, reactive blue 3G, reactive blue R, reactive blue BR, reactive turquoise GF, reactive brilliant blue R, reactive black B, fast yellow G, fast yellow 10G, disazo yellow AAA, disazo yellow AAMX, flavane yellow, chromophthal yellow GR, methine yellow GR, methine yellow, sunset yellow lake, anthrapyrimidine yellow, isoindolinone yellow R, quinophthalone yellow, dinitroaniline orange, pyrazolone orange, dianidine orange, persian orange lake, benzimidazolone orange HL, perynone orange, pyranthrone orange, parared, naphthol red FRR, toluidine red, naphthol carmine FB, naphthol red M, naphthol red BS, naphthol red RN, pyrazolone red, permanent red 2B, lithol red, bon lake red C, lake red C, brilliant carmin 6B, brilliant cannin 3B, Bordeaux 10B, von maroon M, brilliant scarlet G, rhodamine 6G lake, mudder lake, thioindigo Bordeaux, naphthol red FGR, brilliant carmin BS, quinacridone magenta, perylene vermillian, naphthol carmin FBB, perylene red BL, chromophthal scarlet, anthrone red, naphthol red F5RK, erythrocin lake, dianthraquinolyl red, perylene red, perylene maroon, benzimidazolone carmin HF4C, perylene scarlet, amaranth lake, quinacridone red E, pyranthron red, rhodamine B lake, methyl violet lake, alizarine maroon lake, quinacridone red, dioxadine violet, thioindigo magenta, Victoria blue lake, Victoria blue 6G lake, phthalocyanine blue, alkali blue G, indanthrone blue, brilliant green lake, malachite green lake, phthalocyanine green, pigment green B, phthalocyanine green 6Y, benzimidazolone brown HFR, aniline black, dialilide yellow H10G, dialilide yellow HR, carbazole violet, metacresol purple, bromophenol blue, crystal violet, gentiana violet, bromocresol green, bromothimol blue, etc. can be mentioned.

Particularly preferred dyes include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. The color of the inventive adhesive may be additionally imparted by a sensitizing compound.

The color change in the inventive adhesive is initiated by light. Preferably the adhesive's color change is initiated using actinic radiation, using, e.g., a dental curing light which emits visible or near infrared (IR) light for a sufficient amount of time. The mechanism that initiates the color change in the compositions of the invention may be separate from or substantially simultaneous with the curing mechanism that hardens the resin. Thus, e.g., an adhesive may cure (harden) when polymerization is initiated chemically (redox) or thermally, and the color change from an initial color to a final color may occur subsequent to the hardening process upon exposure to actinic radiation.

The change in adhesive color from its initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of greater than about 20; more preferably, $\Delta E^*$ is greater than about 30; most preferably $\Delta E^*$ is greater than about 40.

The inventive orthodontic adhesives include a hardenable resin. The adhesive comprises about 10% to 40%, preferably 15% to 35%, more preferably 20% to 30% of the hardenable resin. The resin, in the presence of a hardener, is capable of being hardened to form a polymer network such as, e.g., acrylate resins, methacrylate resins, or mixtures thereof. Preferably, the hardenable resin is made from one or more matrix-forming oligomer, monomer, or polymer, or blend thereof.

The hardenable resin should be suitable for use in the oral environment, i.e., non-toxic. Preferably, the resin is made from an organic resin having sufficient strength and hydrolytic stability.

Examples of suitable resins include acrylate, methacrylate, urethane, and carbamoylisocyanurate resins, e.g., those shown in U.S. Pat. Nos. 3,066,112; 3,539,533; 3,629,187; 3,709,866; 3,751,399; 3,766,132; 3,860,556; 4,002,669; 4,115,346; 4,259,117; 4,292,029; 4,308,190; 4,327,014; 4,379,695; 4,387,240 and 4,404,150, and mixtures and derivatives thereof.

One class of preferred hardenable resins is materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable groups may be used.

In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (curing), an initiation system or hardener can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 1200 nm.

A variety of visible or near-IR photoinitiator systems may be used for photopolymerization of free-radically polymerizable materials useful in the invention. For example, in free radical polymerization (curing), a photoinitiation system can be selected from systems which initiate polymerization via a two component system of an amine and an α-diketone as described in U.S. Pat. No. 4,071,424, which is herein incorporated by reference. Alternatively and preferably, the resin can be combined with a three component or ternary photoinitiator system such as described in U.S. Pat. No. 5,545,676. A preferred initiator system comprises a sensitizer (which may or may not impart color) and an electron donor. Optionally the initiator system may further comprise an onium salt, thus making the initiator system a ternary system.

The three components of a photoinitiator system are present in the compositions of the invention in "photochemically effective amounts"; that is, amounts of each component sufficient to enable the monomer to undergo photochemical gelation or curing upon exposure to light of the desired wavelength.

In the ternary photoiniator system, the first component is an iodonium salt, e.g., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate, and diphenyliodonium tetrafluoroborate.

The second component in a ternary photoinitiator system is a sensitizer. Preferably, the sensitizer is soluble in the monomer, and is capable of light absorption somewhere within the range of wavelengths of greater than 400 to about 1200 nanometers, more preferably greater than 400 to about 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313. Preferably, in addition to passing this test, a sensitizer is also selected based in part upon shelf stability considerations. Accordingly, selection of a particular sensitizer may depend to some extent upon the particular monomer, oligomer or polymer, the iodonium salt, and the donor chosen.

The sensitizer may also impart a photobleachable color in addition to the color imparted by the dye or pigment colorant. For example, camphorquinone can impart a yellow color to the materials of the invention and Rose Bengal can impart a reddish color to the materials.

Suitable sensitizers can include compounds in the following categories: ketones, coumarin dyes (e.g., ketocoumarins), xanthene dyes, fluorone acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Xanthene dyes include those dyes whose molecular structure is related to xanthene and have a Color Index number ranging from 45000–45999. Ketones (e.g., monoketones or alpha-diketones), ketocoumarins, aminoarylketones and p-substituted aminostyryl ketone compounds are preferred sensitizers. For applications requiring high sensitivity, it is preferred to use a sensitizer containing a julolidinyl moiety. For applications requiring deep cure (e.g., cure of highly-filled composites), it is preferred to use sensitizers having an extinction coefficient below about 1000, more preferably below about 100, at the desired wavelength of irradiation for photopolymerization. Alternatively, dyes that exhibit reduction in light absorption or photobleaching at the excitation wavelength upon irradiation can be used.

For example, a preferred class of ketone sensitizers has the formula:

$$ACO(X)_bB$$

where X is CO or $CR^5 R^6$, where $R^5$ and $R^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, e.g., amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676.

Alternatively, free-radical initiators useful in the invention include the class of acylphosphine oxides, as described in European Patent Application No. 173567, U.S. Pat. No. 4,737,593 and United Kingdom Patent. No. GB 2,310,855. Such acylphosphine oxides are of the general formula $$(R^9)_2-P(=O)-C(=O)-R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocy-clic group, or a $-Z-C(=O)-P(=O)-(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. The terms "lower alkyl" and "lower alkoxy" mean such groups having from 1 to 4 carbon atoms. Most preferably, the acylphosphine oxide is bis(2,4,6-trimethylbenzoyl)phenyl phosphine oxide (IRGACURE™ 819, available from Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be used in catalytically-effective amounts, such as from about 0.1 to 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to about 1200 nanometer include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4, 6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the inventive adhesive includes the class of ionic dye—counterion complex initiators comprising a borate anion and a complementary cationic dye. Borate salt photoinitiators are described, for example, in U.S. Pat. Nos. 4,772,530, 4,954,414, 4,874,450, 5,055,372, and 5,057,393. A borate salt photoinitiator may also use photobleachable sensitizing colorants.

Borate anions useful in these photoinitiators generally can be of the formula:

$$R^1R^2R^3R^4B^-$$

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure initiators." They are typically supplied as two-part systems in which the reactants are stored apart from each other and then combined immediately prior to use.

In a further alternative, heat or thermal energy may be used to initiate the curing, or polymerization, of free radically active groups in the presence of free radical-generating thermal initiators. Examples include peroxides such as, for example, benzoyl peroxide and lauryl peroxide, and azo compounds such as, for example, 2,2-azobis-isobutyronitrile (AIBN). Examples of heat sources suitable for the dental materials of the invention include inductive, convective, and radiant. Thermal sources should be capable of generating temperatures of at least 40° C. to 150° C. under normal conditions or at elevated pressure. This procedure is preferred for initiating polymerization of materials occurring outside of the oral environment.

The initiator compounds are preferably provided in the inventive adhesive in an amount effective to initiate or enhance the rate of cure of the resin system. Photopolymerizable compositions useful in the invention are prepared by simply admixing, under "safe light" conditions, the components as described above. Suitable inert solvents may be used, if desired, when effecting this mixture. Any solvent may be used that does not react appreciably with the adhesive components. Examples of suitable solvents include acetone, dichloromethane, and acetonitrile. A liquid material to be polymerized may be used as a solvent for another liquid or solid material to be polymerized.

The inventive adhesive may optionally comprise additional adjuvants suitable for use in the oral environment, including flavorants, anti-microbials, fragrance, stabilizers, viscosity modifiers, rheology modifiers, fillers and fluoride releasing materials. For example, a fluoride releasing glass may be added to the materials of the invention to provide the benefit of long-term release of fluoride. Fluoroaluminosilicate glasses are suitable for the invention, such as a silanol treated fluoroaluminosilicate glass fillers, as described in U.S. Pat. No. 5,332,429. Organic fluoride sources are also suitable for the invention, such as those described in U.S. Pat. No. 4,871,786. Other suitable adjuvants include agents that impart fluorescence and/or opalescence.

The adhesive can be made by first mixing the hardenable resin with the hardener and colorants. The filler, which was made by conventional processes, is then added. Typically, the entire mixing process is done under conditions that minimize the exposure of the components to visible and infrared light.

A method of making precoated orthodontic appliance of this invention is described in U.S. Pat. No. 5,552,177 (Jacobs et al.). That patent discloses a method for applying adhesive to a base of an orthodontic appliance comprising the following steps: (a) placing a quantity of adhesive onto a carrier; (b) cooling at least a portion of the adhesive to a temperature below ambient, (c) contacting the base of the appliance with the adhesive; and (d) disengaging the adhesive from the carrier while the temperature of the portion of the adhesive is below ambient. It is further disclosed that cooling at least a portion of the adhesive facilitates automated handling of the adhesive and enhances trimming away excess adhesive to leave a precise quantity on the appliance. In this way, the dental practitioner spends minimal time and labor, if any, during installation of the appliance to the patient's teeth. The patent also discloses useful packaging materials that contain a plurality of wells in a substrate. The wells are of suitable size and dimensions to hold the appliances. After the wells are filled with the appropriate number of appliances, a lid is used to cover the wells. Suitable lid materials include, e.g., polyester, metallized films, foils, and film laminates. The entire packaging material should provide barriers to the transmission of light, water vapor, and oxygen. U.S. Pat. Nos. 5,015,180; 5,172,809; 5,354,199; and 5,429,299 also describe adhesive pre-coated orthodontic appliances.

Other useful packaging materials are disclosed in U.S. Pat. No. 5,762,192 (Jacobs et al.); U.S. Pat. No. 5,538,129 (Chester et al.); U.S. Pat. No. 5,348,154 (Jacobs et al.); U.S. Pat. No. 5,328,363 (Chester et al.); and U.S. Pat. No. 5,221,202 (James). In particular, illustrative packaging materials suitable for use in the present invention are disclosed in U.S. Pat. No. 5,772,192 at columns 2 and 3. The packaging materials keep the adhesive and the orthodontic appliances precoated with the adhesive stable at room temperature (about 22° to 26° C.) for at least 6 months, preferably at least 12 months, and at refrigerated temperature (about 35° to 45° C.) for at least 12 months, preferably at least 18 months.

Dispensing a desired amount of adhesive directly onto the base of the orthodontic appliance is another useful method. The adhesive can be dispensed using fine tipped dental instruments, such as direct extrusion through a syringe, brushes, or a disposable unit-dose delivery system. Once adhesive is placed on the orthodontic appliance, the appliance can be applied to the desired teeth surface. Excess adhesive (commonly referred to as "flash") is then removed. The adhesive can then be exposed to actinic radiation to initiate the change in color from its initial color to a final color. Hardening or curing of the composition may occur simultaneously with the color change. In a preferred adhesive that comprises a photoinitiator system, the color change and curing can be accomplished using for example, a dental curing light. If alternative adhesives are thermally or redox cured, the color change may not occur until exposed to actinic radiation.

The inventive adhesive can also be used in indirect bonding methods, as disclosed in U.S. Pat. No. 5,971,754 (Sondhi et al.). In very brief summary, the method involves the following acts. First, an impression of the patient's dental arch is taken. A model is made from the impression using plaster of Paris or "stone" model. A thin layer of separating medium is applied to the stone model and allowed to dry. A pencil mark is made across the labial surface of each replica tooth to assist in subsequent placement of orthodontic appliances. Using the inventive adhesive, the appliance is bonded to the replica tooth. The stark color contrast between the adhesive and the replica tooth providing for easy removal of excess flash and would be consistent with the orthodontist's goal of minimizing working time. Subsequent processing steps in the indirect bonding method can be found in the U.S. Pat. No. 5,971,754 patent, and includes, e.g., making a transfer tray by placing a matrix material (e.g, Bioplast brand clear plastic sheet from Scheu Dental) over the model and appliances and using heat to soften the matrix material.

Conditioning a tooth surface may enhance adhesion of the orthodontic appliance to the tooth or teeth surface(s). Preferable the surfaces can be etched or primed prior to applying the adhesive. Preferably, an etching composition and/or priming composition are used at the locations on the tooth surface that a practitioner desires to place the materials of the present invention. Alternatively or in addition to using an etching composition, an air abrasion system may be used.

The adhesive can be photo-bleached using a variety of methods. It is convenient to use light sources that emit ultraviolet or visible light such as quartz halogen lamps, tungsten-halogen lamps, mercury lamps, plasma arcs, light emitting diodes and lasers.

Color Test

Initial and final colors were determined using a StellarNet Portable Spectrometer Model EPP2000C equipped with a 400 μm fiber reflectance probe and SpectraWiz CIELAB colorimeter software (StellarNet, Inc., Oldsmar, Fla.).

To prepare samples, a small amount of adhesive is extruded onto a polyester liner at the bottom of a 1-inch diameter metal ring. A second liner is placed on top of the adhesive and the adhesive pressed between two plexiglass plates. The metal ring controls the thickness to 0.040 inches. In the case of uncured adhesive, the top plexiglass plate is removed. The sample is placed on top of a white reflectance standard (i.e., a white background). The fiberoptic probe is positioned 0.25 inches above the sample at a 45° angle. Sample time was 1500 milliseconds. Color measurements are taken through the top polyester liner.

The cured samples were -prepared in the same manner except that the adhesive was cured while held between the two plexiglass plates for 3 minutes in a TRIAD 2000 light curing oven (Dentsply International, Inc., York, Pa.). The cured adhesive disk was removed from the mold and placed directly onto the white reflectance standard. The 0.25 inch distance and 45° angle were maintained.

The L*a*b* system is based on a 3-dimensional color space with the positive X-axis representing red, the negative X-axis representing green, the positive Y-axis representing yellow, the negative Y-axis representing blue, and the Z-axis going from zero (black) to 100 (white) with the origin at 50. ΔE* is a calculation of total color change in the three color dimensions and is described by the following equation:

$$\Delta E^* = \text{Square root}((L_1^* - L_2^*)^2 + (a_1^* - a_2^*)^2 + (b_1^* - b_2^*)^2)$$

where subscripts "1" indicates initial state and "2" indicates final state.

All patents referenced herein are incorporated by reference, unless otherwise noted. The following examples are offered to aid in understanding the invention and are not to be construed as limiting the scope of the invention. Unless otherwise indicated, all parts and percentages are by weight.

EXAMPLES

Preparation of Silane-treated Quartz Filler

A 58.3 g portion of deionized water is weighed into a 1000-mL beaker. The water is preheated to about 29° to 33° C. While the water is being stirred with a magnetic stirrer, 105 g quartz filler (available from Coleman Quartz, Jessieville, AK.) was added to the water. Then, about 1.7 g of R-972 AEROSIL silica (available from Degussa, Dublin, Ohio.) was added slowly to the quartz slurry. Using 1% trifluoroacetic acid (available from Aldrich Chemical Co., Milwaukee, Wis.), the pH of the slurry was adjusted to between about 2.5 and 3.0. Mixing continued for another five minutes. About 3 g of 3-methacryloxypropyltrimethoxysilane (available from United Chemical Technologies, Inc., Bristol, Pa.) was added to the slurry. The slurry was stirred for two hours, after which it was poured evenly into a tray to a depth of about 0.125 to 0.5 inch (3.2 to 12.7 mm). The tray was previously lined with a polyester sheet. The tray containing the slurry was placed in a convection drying oven for 12 hours at about 60° C. to yield a dry cake. At the end of the drying cycle, the dried cake was crushed using a mortar and pestle. The crushed filler was dried for 8 hours at about 60° C. The crushed filler was screened though a 74 micrometer nylon screen.

Examples 1 to 8

Various formulations of the inventive adhesive were made as follows. First, a resin precursor was made. The filler, made above, was then mixed thoroughly in resin precursor to yield the adhesive. The resin precursor was made as follows. About 100 grams of the resin precursor was made by charging the following component, as shown in Table 1 below, into a vessel equipped with a mixer and protected from light. The components used include: bisphenol A diglycidylether dimethacrylate (BisGMA), Bis(2-hydroxyethyl)bisphenol-A-dimethacrylate (BisEMA, commercially available as DIACRYL 101, available from Akzo Chemicals, Inc., Chicago, Ill.), 2,6-Di-tert-butyl-4-methylphenol (BHT), camphorquinone (CPQ), ethyl-4-dimethylaminobenzoate (EDMAB), diphenyliodium hexafluorophosphate (DPIHFP), and Erythrosin Yellow blend (EYB, which is a blend of 90 parts by wt Erythrosin and 10 parts by wt Eosin Y). Numerical values in Table 1 are all parts by wt, based on the total weight of the precursor resin.

TABLE 1

| | Components For Precursor Resin | | | | | | |
|---|---|---|---|---|---|---|---|
| Example | BisGMA | BisEMA | EDMAB | DPIHFP | CPQ | BHT | EYB |
| 1 | 58.81 | 39.21 | 0.98 | 0.59 | 0.24 | 0.08 | 0.10 |
| 2 | 59.07 | 39.53 | 0.61 | 0.40 | 0.24 | 0.08 | 0.08 |
| 3 | 59.21 | 38.66 | 1.23 | 0.45 | 0.306 | 0.123 | 0.03 |
| 4 | 59.03 | 38.43 | 1.20 | 0.74 | 0.306 | 0.122 | 0.03 |
| 5 | 60.00 | 39.20 | 0.25 | 0.20 | 0.24 | 0.08 | 0.05 |
| 6 | 59.07 | 39.38 | 0.98 | 0.20 | 0.24 | 0.08 | 0.05 |
| 7 | 58.79 | 39.99 | 0.25 | 0.60 | 0.24 | 0.08 | 0.05 |
| 8 | 58.77 | 39.30 | 0.98 | 0.59 | 0.24 | 0.08 | 0.05 |

The filler was added to the precursor resin such that the adhesive contained 75 parts by wt filler and 25 parts by wt precursor resin. Each sample was subjected to the Color Test described above and the results are shown in Table 2.

TABLE 2

Color Measurements

| Example | Initial L*a*b* color | Final L*a*b* color | ΔE* |
|---|---|---|---|
| 1 | 28.98/38.04/−4.60 | 68.39/5.55/19.59 | 56.52 |
| 2 | 32.17/39.71/−4.13 | 68.29/7.75/22.90 | 55.29 |
| 3 | 35.01/35.41/−6.86 | 75.45/0.81/9.92 | 55.80 |
| 4 | 35.22/36.25/−8.06 | 76.49/0.77/10.24 | 57.42 |
| 5 | 38.15/34.74/−6.77 | 81.39/2.05/11.90 | 57.33 |
| 6 | 36.67/36.63/−5.92 | 76.53/4.18/15.70 | 55.76 |
| 7 | 38.68/29.54/−4.54 | 73.11/2.49/6.18 | 45.07 |
| 8 | 36.76/34.41/−6.08 | 76.15/2.48/11.62 | 53.71 |

As Table 2 indicates, all samples had a color change of ΔE* of greater than 45 from the initial uncured state to the final photo-bleached state and thus are useful for this invention.

What is claimed is:

1. An article comprising:
   an orthodontic appliance having a base for bonding the appliance to a tooth; and
   an adhesive on the base of the appliance, the adhesive comprising a filler, a hardenable resin, a hardener, and a photobleachable dye, wherein the hardener comprises a sensitizing compound different from the photobleachable dye, and wherein the adhesive has an initial color prior to exposure to actinic radiation and a final color subsequent to exposure to actinic radiation, the initial color being different than the final color.

2. The article of claim 1 wherein the adhesive comprises:
   about 70% by weight to about 80% by weight filler;
   about 20% by weight to about 30% by weight hardenable resin;
   about 0.01% by weight to about 1% by weight hardener; and
   about 0.01% by weight to about 1% by weight photobleachable dye.

3. An article comprising:
   an orthodontic appliance having a base for bonding the appliance to a tooth; and
   an adhesive on the base of the appliance, the adhesive comprising:
      about 70% by weight to about 80% by weight filler comprising quartz and fumed silica;
      about 20% by weight to about 30% by weight hardenable resin comprising bisphenol A diglycidylether dimethacrylate and bis(2-hydroxylethyl)bisphenol-A-dimethacrylate;
      about 0.01% by weight to about 1% by weight hardener comprising camphorquinone, ethyl-4-dimethylaminobenzoate, and diphenyliodonium hexafluorophosphate; and
      about 0.01% by weight to about 1% by weight photobleachable dye comprising Erythrosin Yellow blend.

4. The article of claim 1 wherein the change in color from the initial color to the final color has a ΔE* value greater than about 30.

5. The article of claim 1 wherein the hardener comprises a sensitizing compound, an electron donor, and an iodonium salt.

6. The article of claim 1 wherein the photobleachable dye is selected from the group consisting of Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

7. The article of claim 1 wherein the hardenable resin is nontoxic and selected from the group consisting of acrylate resins, methacrylate resins, urethane resins, carbamoylisocyanurate resins, and combinations thereof.

8. The article of claim 1 wherein the final color is a tooth-like color or able to transmit the color of an underlying surface.

9. The article of claim 1 packaged in a container that provides barriers to the transmission of light, water vapor, and oxygen.

10. A kit comprising:
    an orthodontic appliance having a base for bonding the appliance to a tooth;
    an adhesive comprising a filler, a hardenable resin, a hardener, and a photobleachable dye, wherein the hardener comprises a sensitizing compound different from the photobleachable dye, and wherein the adhesive has an initial color prior to exposure to actinic radiation and a final color that is different from the initial color subsequent to the adhesive being exposed to actinic radiation; and
    instructions for using the adhesive and the appliance.

11. The kit of claim 10 further comprising an etching composition.

12. The kit of claim 10 further comprising a priming composition.

13. The kit of claim 10 wherein the adhesive is precoated on the base of the orthodontic appliance.

14. The kit of claim 10 wherein the adhesive is stored in a container selected from the group consisting of a vial, a syringe, and a disposable delivery system.

15. A method of bonding an orthodontic appliance to a tooth comprising:
    providing an orthodontic appliance having a base for bonding the appliance to a tooth and an adhesive on the base, the adhesive having an intial color and comprising a filler, a hardenable resin, a hardener, and a photobleachable dye, wherein the hardener comprises a sensitizing compound different from the photobleachable dye;
    applying the base of the appliance to the tooth surface; and
    exposing the adhesive to actinic radiation, wherein the adhesive has a final color subsequent to the adhesive being exposed to actinic radiation that is different from the initial color of the adhesive.

16. The method of claim 15 wherein the tooth has a color, and the color difference, in terms of ΔE*, between the adhesive initial color and the color of the tooth is greater than about 40.

17. The method of claim 16 wherein applying further comprises forming excess adhesive on the tooth surface.

18. The method of claim 17 further comprising removing the excess adhesive before the adhesive is exposed to actinic radiation.

19. The method of claim 15 wherein the change in color from the initial color to the final color has a ΔE* value greater than about 30.

20. The method of claim 15 further comprising conditioning the tooth surface before applying the base of the appliance to the tooth surface.

21. The method of claim 20 wherein the conditioning comprises treating the tooth surface with an etching composition or a priming composition.

22. A method of bonding an orthodontic appliance to a tooth comprising:

provinding an orthodontic appliance having a base for bonding the appliance to a tooth;

applying an adhesive to the base, the adhesive having an intial color and comprising a filler, a hardenable resin, a hardener, and a photobleachable dye, wherein the hardener comprises a sensitizing compound different from the photobleachable dye;

applying the base of the appliance to the tooth surface; and exposing the adhesive to actinic radiation, wherein the adhesive has a final color subsequent to the adhesive being exposed to actinic radiation that is different from the initial color of the adhesive.

23. The method of claim 22 wherein applying the adhesive comprises applying the adhesive from a container selected from the group consisting of a vial, a syringe, and a disposable delivery system.

24. A method of bonding an orthodontic appliance to a tooth comprising:

providing an orthodontic appliance having a base for bonding the appliance to a tooth;

applying an adhesive to the tooth, the adhesive having an initial color and comprising a filler, a hardenable resin, a hardener, and a photobleachable dye, wherein the hardener comprises a sensitizing compound different from the photobleachable dye;

applying the base of the appliance to the adhesive on the tooth surface; and exposing the adhesive to actinic radiation, wherein the adhesive has a final color subsequent to the adhesive being exposed to actinic radiation that is different from the initial color.

25. The method of claim 24 wherein applying the adhesive comprises applying the adhesive from a container selected from the group consisting of a vial, a syringe, and a disposable delivery system.

* * * * *

UNITED STATES PATENT AND TRADEMARK OFFICE
CERTIFICATE OF CORRECTION

PATENT NO.    : 6,528,555 B1
DATED         : March 4, 2003
INVENTOR(S)   : Nikutowski, Enrique A.

It is certified that error appears in the above-identified patent and that said Letters Patent is hereby corrected as shown below:

<u>Title page,</u>
Item [75], Inventors, the following inventor should be added -- Joel D. Oxman, Minneapolis, MN (US) --

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,528,555 B1
DATED          : March 4, 2003
INVENTOR(S)    : Nikutowski, Enrique A.

It is certified that error appears in the above-identified patent and that said Letters Patent is hereby corrected as shown below:

<u>Title page,</u>
Item [56], References Cited, OTHER PUBLICATIONS, delete "Pharmacueticals" and insert in place thereof -- Pharmaceuticals --
Item [57], ABSTRACT,
Line 7, delete "on to" and insert in place thereof -- onto --

<u>Column 1,</u>
Line 7, delete "relates adhesive" and insert in place thereof -- relates to an adhesive --
Line 65, delete "(tricholormethyl)" and insert in place thereof -- (trichloromethyl) --

<u>Column 2</u>
Line 5, delete "exhibits" and insert in place thereof -- exhibit --.

<u>Column 4,</u>
Line 28, delete "IIB" in the first instance and insert in place thereof -- IB --.
Line 29, delete "IIB" and insert in place thereof -- IIIB --.

<u>Column 5,</u>
Line 35, delete "Ginea" and insert in place thereof -- Guinea --.
Line 42, delete "azaline" and insert in place thereof -- alizarin --.
Line 43, delete "SR" and insert in place thereof -- 5R --.
Line 63, delete "brighter" and insert in place thereof -- brightener --.

<u>Column 6,</u>
Line 10, delete "bon".
Lines 11, 14, 15, 18, delete "carmin" and insert in place thereof -- carmine --.
Line 11, delete "cannin" and insert in place thereof -- carmine --.
Line 26, in both instances, delete "dialilide" and insert in place thereof -- diarilide --.

<u>Column 8,</u>
Line 15, delete "photoiniator" and insert in place thereof -- photoinitiator --.

<u>Column 9,</u>
Line 36, delete "2,2'- 3 3'-" and insert in place thereof -- 2,2'- 3,3' --.

UNITED STATES PATENT AND TRADEMARK OFFICE
CERTIFICATE OF CORRECTION

PATENT NO. : 6,528,555 B1
DATED : March 4, 2003
INVENTOR(S) : Nikutowski, Enrique A.

It is certified that error appears in the above-identified patent and that said Letters Patent is hereby corrected as shown below:

Column 12,
Line 19, delete "5,354,199; and 5,429,299" and insert in place thereof
-- and 5,354,199 --.
Line 27, delete "5,772,192" and insert in place thereof -- 5,762,192 --.
Line 63, delete "providing" and insert in place thereof -- provides --.

Column 13,
Lines 5-6, delete "Preferable" and insert in place thereof -- Preferably --.
Line 33, delete "-prepared" and insert in place thereof -- prepared --.

Column 14,
Line 13, delete "AK" and insert in place thereof -- AR --.
Line 30, delete "though" and insert in place thereof -- through --.
Line 48, delete "diphenyliodium" and insert in place thereof -- diphenyliodonium --.

Column 16,
Line 42, delete "intial" and insert in place thereof -- initial --.

Column 17
Line 9, delete "intial" and insert in place thereof -- initial --.

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,528,555 B1
DATED         : March 4, 2003
INVENTOR(S)   : Nikutowski, Enrique A.

It is certified that error appears in the above-identified patent and that said Letters Patent is hereby corrected as shown below:

Column 5,
Line 34, "poral yellow 5G" should read -- Polar Yellow 5G --.

Signed and Sealed this

Nineteenth Day of April, 2005

JON W. DUDAS
*Director of the United States Patent and Trademark Office*